(12) United States Patent   (10) Patent No.: US 11,345,955 B2
Badenhorst et al.   (45) Date of Patent: May 31, 2022

(54) HYBRIDIZATION-EXTENSION-LIGATION STRATEGY FOR GENERATING CIRCULAR SINGLE-STRANDED DNA LIBRARIES

(71) Applicants: Roche Sequencing Solutions, Inc., Pleasanton, CA (US); Kapa Biosystems, Inc., Wilmington, MA (US)

(72) Inventors: Daleen Badenhorst, Wellington (CA); Richard Dannebaum, Pleasant Hill, CA (US); Ashley Hayes, San Francisco, CA (US); Monica Herrera, Livermore, CA (US); Severine Margeridon, Castro Valley, CA (US); Martin Ranik, Cape Town (ZA)

(73) Assignees: ROCHE SEQUENCING SOLUTIONS, INC., Pleasanton, CA (US); KAPA BIOSYSTEMS, INC., Wilmington, MA (US)

( * ) Notice: Subject to any disclaimer, the term of this patent is extended or adjusted under 35 U.S.C. 154(b) by 180 days.

(21) Appl. No.: 16/813,379

(22) Filed: Mar. 9, 2020

(65) Prior Publication Data

US 2020/0199663 A1   Jun. 25, 2020

Related U.S. Application Data

(63) Continuation of application No. PCT/EP2018/074941, filed on Sep. 14, 2018.
(Continued)

(51) Int. Cl.
    *C12P 19/34*   (2006.01)
    *C12Q 1/6851*   (2018.01)
    (Continued)

(52) U.S. Cl.
    CPC ....... *C12Q 1/6851* (2013.01); *C12N 15/1065* (2013.01); *C12Q 1/6869* (2013.01)

(58) Field of Classification Search
    CPC .................................................. C12Q 1/6869
    See application file for complete search history.

(56) References Cited

U.S. PATENT DOCUMENTS

| 2011/0294689 A1 | 12/2011 | Namsaraev |
| 2012/0003657 A1* | 1/2012 | Myllykangas ....... C12Q 1/6869 435/6.12 |

(Continued)

FOREIGN PATENT DOCUMENTS

| WO | WO2010051773 A1 | 5/2010 |
| WO | WO2012003374 A2 | 1/2012 |

(Continued)

OTHER PUBLICATIONS

International Search Report and Written Opinion, dated Nov. 29, 2018, in corresponding PCT/EP2018/074941, filed Sep. 14, 2018, pp. 1-17.

*Primary Examiner* — Kenneth R Horlick

(74) *Attorney, Agent, or Firm* — Eric Grant Lee; Olga Kay

(57) ABSTRACT

The invention is a novel method of making and using a library such as a sequencing library of single stranded circular nucleic acid templates via splint ligation. In particular, disclosed are methods of making circular target nucleic acid molecules and libraries of such molecules for downstream analysis such as nucleic acid sequencing. The method comprises the steps of adding universal sequences to nucleic acid molecules, rendering single-stranded these nucleic acid molecules with universal sequences on their ends by contacting with a probe complementary to at least a portion of the universal sequences, and allowing the (Continued)

hybridized probe to enable circularization and formation of single-stranded circular (sscDNA) molecules.

8 Claims, 9 Drawing Sheets

Specification includes a Sequence Listing.

Related U.S. Application Data

(60) Provisional application No. 62/559,474, filed on Sep. 15, 2017.

(51) Int. Cl.
    *C12N 15/10*     (2006.01)
    *C12Q 1/6869*     (2018.01)

(56) References Cited

U.S. PATENT DOCUMENTS

2015/0284789 A1* 10/2015 Hogers ................ C12Q 1/6806
    506/2
2018/0371006 A1* 12/2018 Kazakov ................ C07H 21/02

FOREIGN PATENT DOCUMENTS

| WO | WO2012162267 A2 | 11/2012 |
| WO | 2013036685 A1 | 3/2013 |
| WO | WO2013036668 A1 | 3/2013 |
| WO | 2014/196863 A1 | 12/2014 |

\* cited by examiner

Fig. 5

Fig. 8 (part 1)
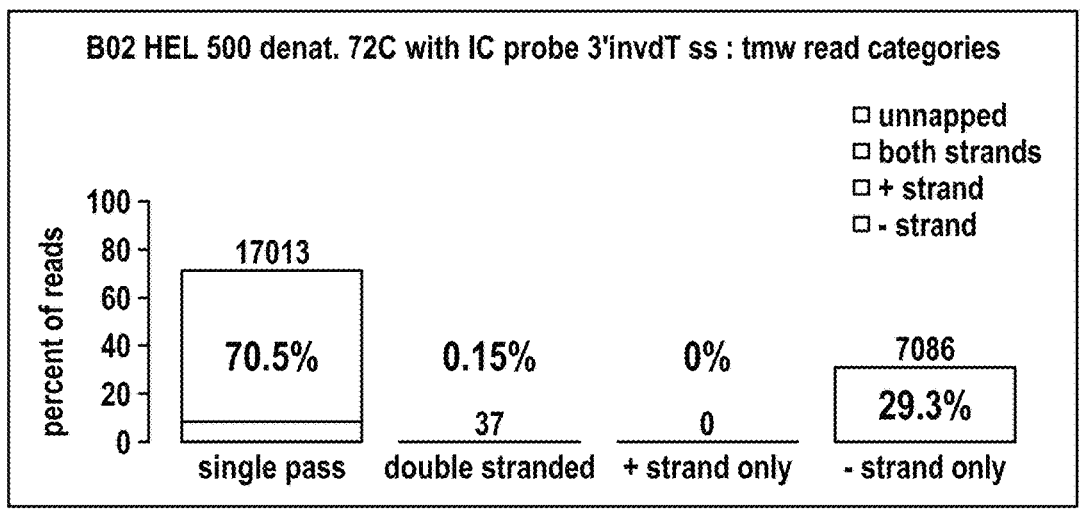
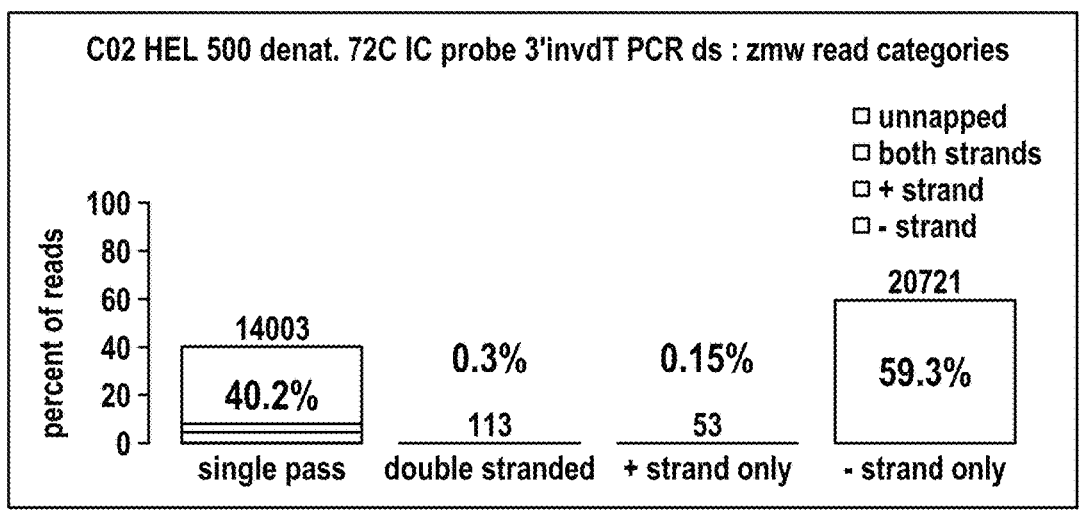
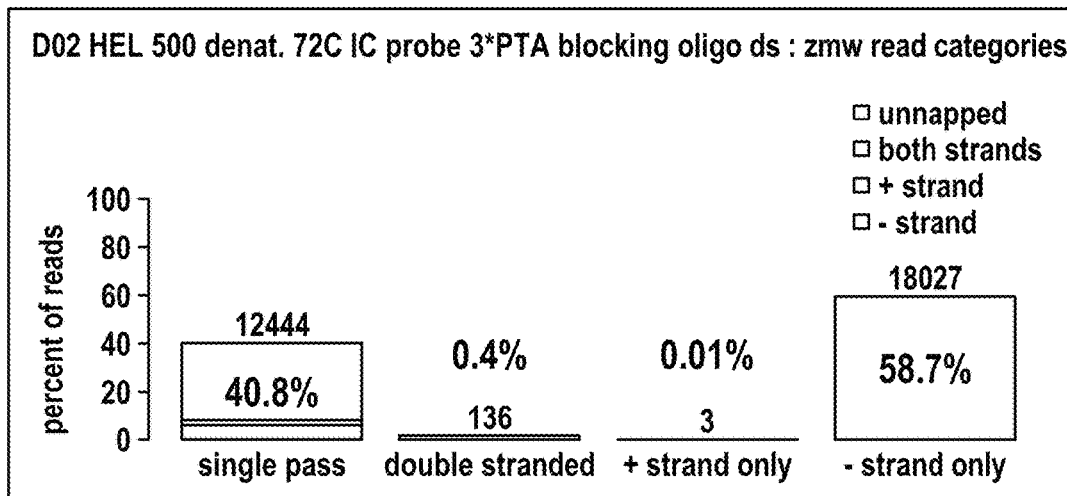

Fig. 8 (part 2)
D
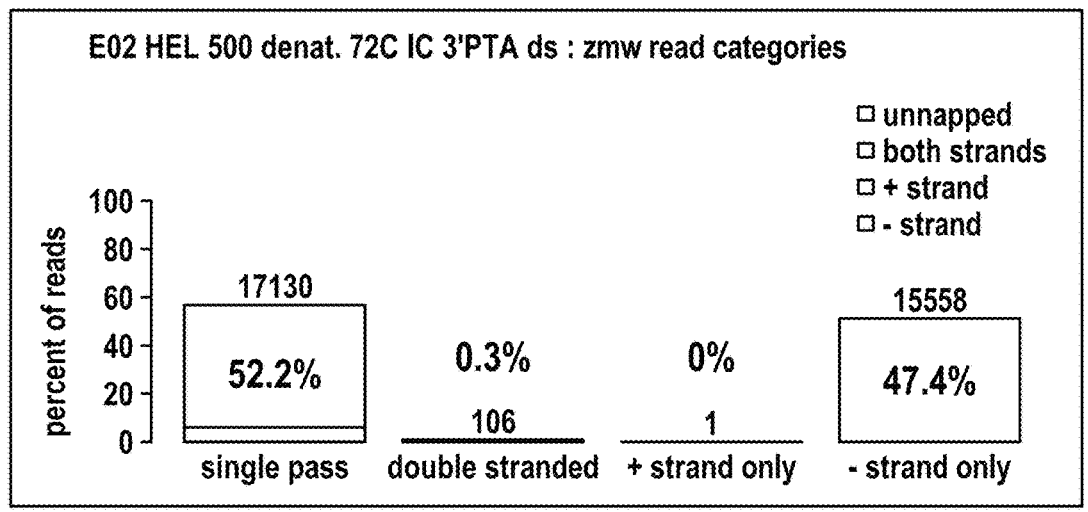
E
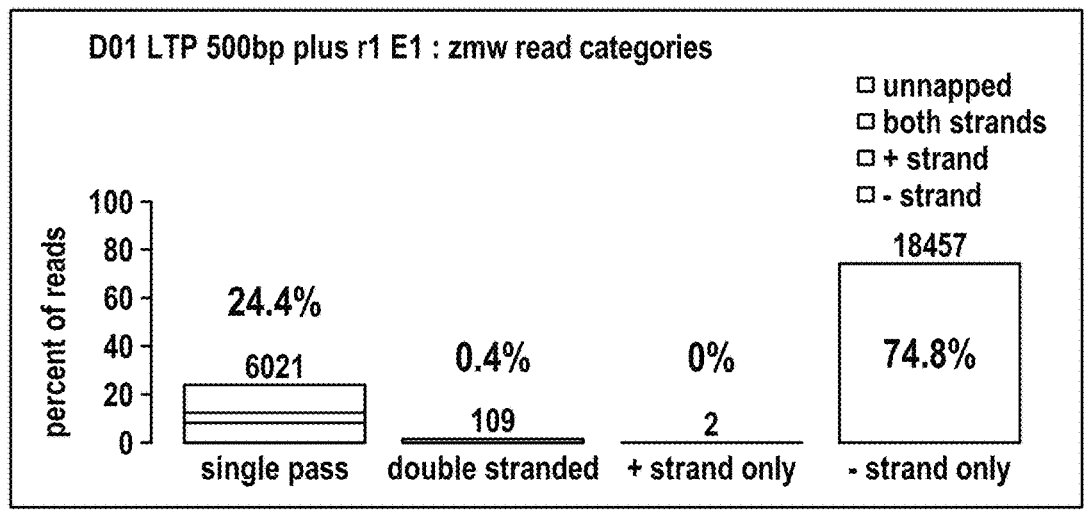

HYBRIDIZATION-EXTENSION-LIGATION STRATEGY FOR GENERATING CIRCULAR SINGLE-STRANDED DNA LIBRARIES

CROSS-REFERENCE TO RELATED APPLICATIONS

This application is a continuation of the International Application Serial No. PCT/EP/2018/074941 filed on Sep. 14, 2018, which claims priority to the U.S. Provisional Application Ser. No. 62/559,474 filed on Sep. 15, 2017 both of which are incorporated herein by reference.

SEQUENCE LISTING INCORPORATION BY REFERENCE

This application contains a Sequence Listing which has been filed electronically in ASCII format and is hereby incorporated by reference in its entirety. Said ASCII copy has a file name of 3442_WO_ST25, is created on Mar. 2, 2020, which is 2,424 bytes in size.

FIELD OF THE INVENTION

The invention relates to the field of nucleic acid analysis and more specifically, to preparing circular templates for nucleic acid sequencing.

BACKGROUND OF THE INVENTION

Circular nucleic acid templates have multiple uses in nucleic acid analysis. Linear nucleic acids are converted into a circular form for amplification, e.g., by rolling circle amplification (RCA) and subsequent detection and quantification, see U.S. Pat. No. RE 44,265. The use of circular templates in sequencing is also known in the art. See U.S. Pat. Nos. 7,302,146 and 8,153,375. Current sequencing strategies require that auxiliary sequences such as primer binding sites and barcodes be introduced into a template. The present invention is a novel efficient method of creating circular nucleic acid templates suitable for sequencing. The method allows the creation of templates of virtually unrestricted length.

SUMMARY OF THE INVENTION

In one embodiment, the invention is a method of forming a circular molecule from a target nucleic acid in a sample, comprising: amplifying the target nucleic acid with a first and second bipartite amplification primers comprising a universal circularization sequence and a target-specific sequence to generate double stranded amplicons; separating the strands of the double stranded amplicons; contacting a strand of the amplicon with a circularization oligonucleotide comprising (i) a 5'-end, (ii) a sequence complementary to the universal circularization sequence in the first amplification primer, (iii) a sequencing primer binding site, (iv) a sequence complementary to the universal circularization sequence in the second amplification primer, (v) an extendable 3'-end; contacting the sample with an extension DNA polymerase to generate a copy strand; and contacting the sample with a DNA ligase to form at least one circular nucleic acid molecule from an amplicon strand or a copy strand.

In some embodiments, the circularization oligonucleotide comprises (i) a 5'-end, (ii) a single stranded region, (iii) a double-stranded stem region, (iv) a single-stranded loop region, (v) a single stranded region, and (vi) 3'-end to generate a hybrid structure wherein the universal circularization sequences in the strand are hybridized to the single stranded regions (ii) and (v) of the circularization oligonucleotide; and step d) comprises extension of the 3'-end of the circularization oligonucleotide to reach the 5'-end of the circularization oligonucleotide; and step e) comprises ligation of the 3'- and 5'end of the circularization oligonucleotide from step d). In some embodiments, the single stranded loop region of the circularization oligonucleotide comprises a primer binding site for a sequencing primer.

In some embodiments the circularization oligonucleotide comprises a 5'-phosphate group and an extension blocking modification at the 3'-end; and step d) comprises (i) extending the 3'-end of the strand of the amplicon from step b) to copy the sequencing primer binding site, and (ii) extending a primer bound to one end of the strand of the amplicon from step b) until it reaches a blocking oligonucleotide hybridized the opposite end of the strand of the amplicon; and step e) comprises self-ligating the extended strand of the amplicon from step d).

In some embodiments, the circularization oligonucleotide comprises a 5'-phosphate group and a nuclease resistant modification at the 3'-end; and step d) comprises (i) extending the 3'-end of the strand of the amplicon from step b) to copy the sequencing primer binding site, and (ii) extending the 3'-end of the circularization oligonucleotide until it reaches a blocking oligonucleotide hybridized the end of the strand of the amplicon; and step e) comprises self-ligating the extended strand of the amplicon from step d).

In some embodiments the circularization oligonucleotide comprises a 5'-phosphate group and a nuclease resistant modification at the 3'-end; and step d) comprises (i) extending the 3'-end of the strand of the amplicon from step b) to copy the sequencing primer binding site, and (ii) extending the 3'-end of the circularization oligonucleotide until it reaches the 5'-end of the circularization oligonucleotide; and step e) comprises self-ligating the extended strand of the amplicon from step d).

In some embodiments, the target nucleic acid comprises fragments of a genome selected from cell-free plasma DNA, sonicated DNA and restriction digested DNA. In some embodiments the universal sequences on the first and second amplification primers are distinct. In some embodiments, only one of the first and second amplification primers comprises a 5'-phosphate group. In some embodiments, the strands of the double stranded amplicons are separated by nuclease digestion or by physical means. In some embodiments, ligation is performed via a ligase selected from Taq DNA ligase and T4 DNA ligase. In some embodiments the circularization oligonucleotide comprises a ligand for a capture moiety, e.g., the ligand-capture moiety pair of biotin-streptavidin, antibody-antigen or oligonudeotide-complementary capture oligonudeotide.

In some embodiments, the invention is a method of making a library of circular target nucleic acids for sequencing comprising: amplifying the target nucleic acids with a first and second bipartite amplification primers comprising a universal circularization sequence and a target-specific sequence to generate double stranded amplicons; separating the strands of the double stranded amplicons; contacting the strands of the amplicons with a circularization oligonucleotides each comprising (i) a 5'-end, (ii) a sequence complementary to the universal circularization sequence in the first amplification primer, (iii) a sequencing primer binding site, (iv) a sequence complementary to the universal circularization sequence in the second amplification primer, (v) an extendable 3'-end; contacting the sample with an extension DNA polymerase to generate a copy strands from amplicon strands; and contacting the sample with a DNA ligase to form a library of circular nucleic acid molecules from amplicon strands or copy strands.

In some embodiments, the invention is a method of determining the sequence of a double-stranded target nucleic acid in a sample comprising: forming circular nucleic acids by a method of claim 1; contacting the sample with a sequencing primer complementary to the sequencing primer binding site; and extending the sequencing primer with a nucleic acid polymerase thereby determining the sequence of the target nucleic acid. In some embodiments, the universal priming sites are attached via ligation of an adaptor comprising the universal priming sites.

In some embodiments, the invention is a method of determining the sequence of a double-stranded target nucleic acid in a sample comprising: forming circular nucleic acids by a method of claim 1 except omitting a sequencing primer binding site from the circularization oligonucleotide; extending the circularization oligonucleotide with a nucleic acid polymerase thereby determining the sequence of the target nucleic acid.

In some embodiments, the invention is a kit for determining the sequence of a target nucleic acid comprising: a first and second bipartite amplification primers comprising a universal circularization sequence and a target-binding sequence; a circularization oligonucleotide comprising (i) a 5'-end, (ii) a sequence complementary to the universal circularization sequence in the first amplification primer, (iii) a sequencing primer binding site, (iv) a sequence complementary to the universal circularization sequence in the second amplification primer, (v) an extendable 3'-end; a DNA polymerase; and a DNA ligase.

BRIEF DESCRIPTION OF THE DRAWINGS

FIG. 5 shows step 4 of the method: annealing of the sequencing primer.

FIG. 8 shows results of sequencing of the templates created using the HEL method.

DETAILED DESCRIPTION OF THE INVENTION

Definitions

Figure 1:
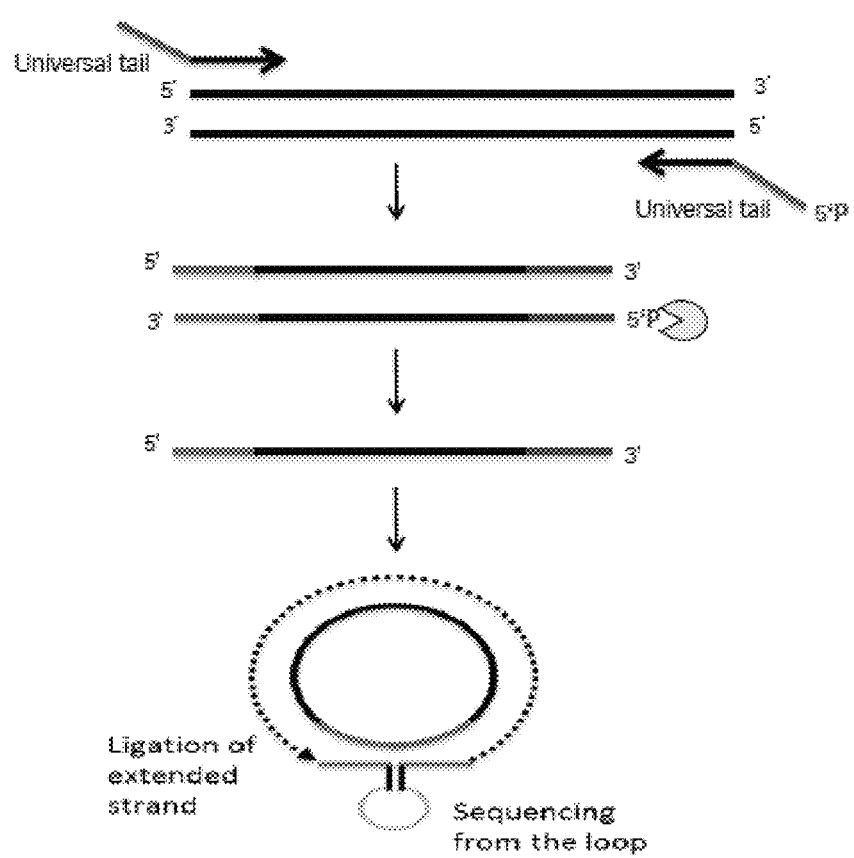
FIG. 1 shows the general scheme of the Hybridization-Extension-Ligation (HEL) method.

The following definitions aid in understanding of this disclosure.

The term "sample" refers to any composition containing or presumed to contain target nucleic acid. This includes a sample of tissue or fluid isolated from an individual for example, skin, plasma, serum, spinal fluid, lymph fluid, synovial fluid, urine, tears, blood cells, organs and tumors, and also to samples of in vitro cultures established from cells taken from an individual, including the formalin-fixed paraffin embedded tissues (FFPET) and nucleic acids isolated therefrom. A sample may also include cell-free material, such as cell-free blood fraction that contains cell-free DNA (cfDNA) or circulating tumor DNA (ctDNA).

The term "nucleic acid" refers to polymers of nucleotides (e.g., ribonucleotides and deoxyribonucleotides, both natural and non-natural) including DNA, RNA, and their subcategories, such as cDNA, mRNA, etc. A nucleic acid may be single-stranded or double-stranded and will generally contain 5'-3' phosphodiester bonds, although in some cases, nucleotide analogs may have other linkages. Nucleic acids may include naturally occurring bases (adenosine, guanosine, cytosine, uracil and thymidine) as well as non-natural bases. Some examples of non-natural bases include those described in, e.g., Seela et al., (1999) Helv. Chim. Acta 82:1640. The non-natural bases may have a particular function, e.g., increasing the stability of the nucleic acid duplex, inhibiting nuclease digestion or blocking primer extension or strand polymerization.

The terms "polynucleotide" and "oligonucleotide" are used interchangeably. Polynucleotide is a single-stranded or a double-stranded nucleic acid. Oligonucleotide is a term sometimes used to describe a shorter polynucleotide. Oligonucleotides are prepared by any suitable method known in the art, for example, by a method involving direct chemical synthesis as described in Narang et al. (1979) Meth. Enzymol. 68:90-99; Brown et al. (1979) Meth. Enzymol. 68:109-151; Beaucage et al. (1981) Tetrahedron Lett. 22:1859-1862; Matteucci et al. (1981) J. Am. Chem. Soc. 103:3185-3191.

The term "primer" refers to a single-stranded oligonucleotide which hybridizes with a sequence in the target nucleic acid ("primer binding site") and is capable of acting as a point of initiation of synthesis along a complementary strand of nucleic acid under conditions suitable for such synthesis.

The term "adaptor" means a nucleotide sequence that may be added to another sequence so as to import additional properties to that sequence. An adaptor is typically an oligonucleotide that can be single- or double-stranded, or may have both a single-stranded portion and a double-stranded portion.

The term "ligation" refers to a condensation reaction joining two nucleic acid strands wherein a 5'-phosphate group of one molecule reacts with the 3'-hydroxyl group of another molecule. Ligation is typically an enzymatic reaction catalyzed by a ligase or a topoisomerase. Ligation may join two single strands to create one single-stranded molecule. Ligation may also join two strands each belonging to a double-stranded molecule thus joining two double-stranded molecules. Ligation may also join both strands of a double-stranded molecule to both strands of another double-stranded molecule thus joining two double-stranded molecules. Ligation may also join two ends of a strand within a double-stranded molecule thus repairing a nick in the double-stranded molecule.

The term "barcode" refers to a nucleic acid sequence that can be detected and identified. Barcodes can be incorporated into various nucleic acids. Barcodes are sufficiently long e.g., 2, 5, 20 nucleotides, so that in a sample, the nucleic acids incorporating the barcodes can be distinguished or grouped according to the barcodes.

The term "multiplex identifier" or "MID" refers to a barcode that identifies a source of a target nucleic acids (e.g., a sample from which the nucleic acid is derived). All or substantially all the target nucleic acids from the same sample will share the same MID. Target nucleic acids from different sources or samples can be mixed and sequenced simultaneously. Using the MIDs the sequence reads can be assigned to individual samples from which the target nucleic acids originated.

The term "unique molecular identifier" or "UID" refers to a barcode that identifies a nucleic acid to which it is attached. All or substantially all the target nucleic acids from the same sample will have different UIDs. All or substantially all of the progeny (e.g., amplicons) derived from the same original target nucleic acid will share the same UID.

The term "universal primer" and "universal priming binding site" or "universal priming site" refer to a primer and primer binding site present in (typically, through in vitro addition to) different target nucleic acids. The universal priming site is added to the plurality of target nucleic acids using adaptors or using target-specific (non-universal) primers having the universal priming site in the 5'-portion. The universal primer can bind to and direct primer extension from the universal priming site.

More generally, the term "universal" refers to a nucleic acid molecule (e.g., primer or other oligonucleotide) that can be added to any target nucleic acid and perform its function irrespectively of the target nucleic acid sequence. The universal molecule may perform its function by hybridizing to the complement, e.g., a universal primer to a universal primer binding site or a universal circularization oligonucleotide to a universal primer sequence.

As used herein, the terms "target sequence", "target nucleic acid" or "target" refer to a portion of the nucleic acid sequence in the sample which is to be detected or analyzed. The term target includes all variants of the target sequence, e.g., one or more mutant variants and the wild type variant.

The term "amplification" refers to a process of making additional copies of the target nucleic acid. Amplification can have more than one cycle, e.g., multiple cycles of exponential amplification. Amplification may also have only one cycle (making a single copy of the target nucleic acid). The copy may have additional sequences, e.g., those present in the primers used for amplification.

The term "sequencing" refers to any method of determining the sequence of nucleotides in the target nucleic acid.

The present invention is a method of making circular target nucleic acid molecules and libraries of such molecules for downstream analysis such as nucleic acid sequencing. As shown in FIG. 1, the method comprises the use an oligonucleotide probe to circularize nucleic acid molecules. First, the nucleic acid molecules have universal sequences added to each end. Nucleic acids with universal sequences at each end are then rendered single stranded and contacted with a probe complementary to at least a portion of the universal sequences. The probe is hybridized to enable circularization and formation of single stranded circular (sscDNA) molecules.

The method has advantages over existing circularization methods, e.g., U.S. Pat. No. RE 44,265 and US2012003657. In contrast to that method, the present method uses a universal circularization sequence attached to the target sequences. The present method does not use a non-target oligonucleotide containing multiple restriction sites inserted between the ends of the target molecule to ensure the presence of restriction sites (see U.S. Pat. No. RE 44,265, FIG. 2 therein). The same strategy is used in US2012003657 (see FIG. 1A therein) where the "vector" oligonucleotide containing sequencing primer binding sites is used. The present invention uses more efficient intramolecular circularization instead of intermolecular ligation with auxiliary oligonucleotides.

The present invention comprises detecting a target nucleic acid in a sample. In some embodiments, the sample is derived from a subject or a patient. In some embodiments the sample may comprise a fragment of a solid tissue or a solid tumor derived from the subject or the patient, e.g., by biopsy. The sample may also comprise body fluids (e.g., urine, sputum, serum, plasma or lymph, saliva, sputum, sweat, tear, cerebrospinal fluid, amniotic fluid, synovial fluid, pericardial fluid, peritoneal fluid, pleural fluid, cystic fluid, bile, gastric fluid, intestinal fluid, and/or fecal samples), The sample may comprise whole blood or blood fractions where tumor cells may be present. In some embodiments, the sample, especially a liquid sample may comprise cell-free material such as cell-free DNA or RNA including cell-free tumor DNA or tumor RNA. In some embodiments, the sample is a cell-free sample, e.g., cell-free blood-derived sample where cell-free tumor DNA or tumor RNA are present. In other embodiments, the sample is a cultured sample, e.g., a culture or culture supernatant containing or suspected to contain an infectious agent or nucleic acids derived from the infectious agent. In some embodiments, the infectious agent is a bacterium, a protozoan, a virus or a mycoplasma.

A target nucleic acid is the nucleic acid of interest that may be present in the sample. In some embodiments, the target nucleic acid is a gene or a gene fragment. In other embodiments, the target nucleic acid contains a genetic variant, e.g., a polymorphism, including a single nucleotide polymorphism or variant (SNP of SNV), or a genetic rearrangement resulting e.g., in a gene fusion. In some embodiments, the target nucleic acid comprises a biomarker. In other embodiments, the target nucleic acid is characteristic of a particular organism, e.g., aids in identification of the pathogenic organism or a characteristic of the pathogenic organism, e.g., drug sensitivity or drug resistance. In yet other embodiments, the target nucleic acid is characteristic of a human subject, e.g., the HLA or KIR sequence defining the subject's unique HLA or KIR genotype. In yet other embodiments, all the sequences in the sample are target nucleic acids e.g., in shotgun genomic sequencing.

In an embodiment of the invention, a double-stranded target nucleic acid is converted into the template configuration of the invention. In some embodiments, the target nucleic acid occurs in nature in a single-stranded form (e.g., RNA, including mRNA, microRNA, viral RNA; or single-stranded viral DNA). The single-stranded target nucleic acid is converted into double-stranded form to enable the further steps of the claimed method.

Longer target nucleic acids may be fragmented although in some applications longer target nucleic acids may be desired to achieve a longer read. In some embodiments, the target nucleic acid is naturally fragmented, e.g., circulating cell-free DNA (cfDNA) or chemically degraded DNA such as the one founds in preserved samples. In other embodiments, the target nucleic acid is fragmented in vitro, e.g., by physical means such as sonication or by endonuclease digestion, e.g., restriction digestion.

In some embodiments, the invention is a method comprising a step of amplifying the target nucleic acid. The amplification may be by polymerase chain reaction (PCR) or any other method that utilizes oligonucleotide primers. Various PCR conditions are described in *PCR Strategies* (M. A. Innis, D. H. Gelfand, and J. J. Sninsky eds., 1995, Academic Press, San Diego, Calif.) at Chapter 14; *PCR Protocols: A Guide to Methods and Applications* (M. A. Innis, D. H. Gelfand, J. J. Sninsky, and T. J. White eds., Academic Press, NY, 1990).

The amplification may utilize first and second bipartite amplification primers comprising a universal circularization sequence and a target-specific sequence to generate double stranded amplicons. (FIG. 2) In some embodiments, a defined target or group of target nucleic acids is being interrogated. In such embodiments, target specific amplification primers may be used. A primer may have a bipartite structure composed of a target-specific sequence in the 3'-portion and a universal sequence in the 5'-portion. Typically, the target-specific primers are used as a pair of distinct oligonucleotides, e.g., a forward and a reverse primer. For subsequent steps, a different universal sequence can be added to the forward and the reverse primer in order to distinguish the complementary strands (i.e., the (+) and the (−) strands) in subsequent steps of the method. In some embodiments, the universal sequence of the bipartite primers comprises a sequencing primer binding site.

In some embodiments, the method comprises a step of target enrichment. Target enrichment can be accomplished by hybridization to nucleic acid probes complementary to the target nucleic acid or a plurality of target nucleic acids. The probes may be conjugated to a capture moiety (capture probes). Target nucleic acids captured with the capture probes are then denatured and eluted from the capture probes and subjected to the downstream steps of the invention. Pre-made and custom-designed capture probes are readily available, e.g., SureSelect probes (Agilent Tech., Santa Clara, Calif.) or SeqCap probes (Roche Sequencing, Madison, Wisc.)

The amplification may also utilize a universal adaptor sequence comprising universal primer binding sites conjugated to the target sequence In other embodiments, a plurality of target nucleic acids is being interrogated, e.g., a whole genome or all nucleic acids present in a sample, e.g., a sample suspected of containing one or more unknown pathogenic organisms. In such embodiments, a target specific primer is not advantageous and a universal primer is used. In such embodiments, a universal primer binding site is added, e.g., by ligation of an adaptor molecule containing a universal primer binding site sequence. Typically, such adaptors are added independent of the sequence of the target nucleic acid, for example, by ligation. In such embodiments, the target nucleic acids receive the same adaptor molecule at each end. To distinguish the strands of the resulting adapted target nucleic acid, the adaptor may have a Y-structure, see e.g., U.S. Pat. Nos. 8,053,192, 8,182,989 and 8,822,150.

In some embodiments of the present invention, the adaptor molecules are ligated to the target nucleic acid. The ligation can be a blunt-end ligation or a more efficient cohesive-end ligation. The target nucleic acid or the adaptors may be rendered blunt-ended by strand-filling, i.e., extending a 3'-terminus by a DNA polymerase to eliminate a 5'-overhang. In some embodiments, the blunt-ended adaptors and target nucleic acid may be rendered cohesive by addition of a single nucleotide to the 3'-end of the adaptor and a single complementary nucleotide to the 3'-ends of the target nucleic acid, e.g., by a DNA polymerase or a terminal transferase. In yet other embodiments, the adaptors and the target nucleic acid may acquire cohesive ends (overhangs) by digestion with restriction endonucleases. The latter option is more advantageous for known target sequences that are known to contain the restriction enzyme recognition site. In each of the above embodiments, the adaptor molecule may acquire the desired ends (blunt, single-base extension or multi-base overhang) by design of the synthetic adaptor oligonucleotides further described below. In some embodiments, other enzymatic steps may be required to accomplish the ligation. In some embodiments, a polynucleotide kinase may be used to add 5'-phosphates to the target nucleic acid molecules and adaptor molecules.

In some embodiments, the adaptor molecules are in vitro synthesized artificial sequences. In other embodiments, the adaptor molecules are in vitro synthesized naturally-occurring sequences known to possess the desired secondary structure. In yet other embodiments, the adaptor molecules are isolated naturally occurring molecules or isolated non naturally-occurring molecules.

In some embodiments, the invention comprises introduction of barcodes into the target nucleic acids. Sequencing individual molecules typically requires molecular barcodes such as described e.g., in U.S. Pat. Nos. 7,393,665, 8,168,385, 8,481,292, 8,685,678, and 8,722,368. A unique molecular barcode is a short artificial sequence added to each molecule in a sample such as a patient's sample typically during the earliest steps of in vitro manipulations. The barcode marks the molecule and its progeny. The unique molecular barcode (UID) has multiple uses. Barcodes allow tracking each individual nucleic acid molecule in the sample to assess, e.g., the presence and amount of circulating tumor DNA (ctDNA) molecules in a patient's blood in order to detect and monitor cancer without a biopsy. See U.S. patent application Ser. Nos. 14/209,807 and 14/774,518. Unique molecular barcodes can also be used for sequencing error correction. The entire progeny of a single target molecule is marked with the same barcode and forms a barcoded family. A variation in the sequence not shared by all members of the barcoded family is discarded as an artifact and not a true mutation. Barcodes can also be used for positional deduplication and target quantification, as the entire family represents a single molecule in the original sample. See Id.

In some embodiments of the present invention, bi-partite amplification primers comprise one or more barcodes. In other embodiments, adaptors comprise one or more barcodes. A barcode can be a multiplex sample ID (MID) used to identify the source of the sample where samples are mixed (multiplexed). The barcode may also serve as a unique molecular ID (UID) used to identify each original molecule and its progeny. The barcode may also be a combination of a UID and an MID. In some embodiments, a single barcode is used as both UID and MID.

In some embodiments, each barcode comprises a predefined sequence. In other embodiments, the barcode comprises a random sequence. Barcodes can be 1-20 nucleotides long.

In some embodiments, the method interrogates only one of the two strands of the target nucleic acid or analyzes the two strands separately. The invention comprises a step of separating the strands of the double stranded amplicons. In some embodiments, one strand is degraded and the other strand is retained for subsequent steps of the method. In some embodiments, the amplicon is subjected to exonuclease treatment (e.g., by a viral exonuclease, T7 or Lambda exonuclease). In some embodiments, the primers or adapters may be modified to include a 5'-nuclease targeting (such as 5'-phosphate) or 3'-end protection (such as a phosphorothioate) to specifically target only one strand for exonuclease digestion. The two strands may also be separated by physical means, i.e., alkaline denaturation or heat denaturation. In yet other embodiments, a desired strand is captured with an affinity reagent capable of selectively binding a strand with the affinity ligand. In some embodiments, a primer is biotinylated and the product of primer extension is captures with streptavidin.

In some embodiments, the ends of the nucleic acid are phosphorylated. In some embodiments, the 5'-end of one primer is phosphorylated in order to effect degradation of one strand with an exonuclease, e.g., Lambda exonuclease.

In other embodiments, the 5'-end of the adaptor is phosphorylated for that purpose. A mixture (e.g., an equal mixture) of phosphorylated and non-phosphorylated adaptors can be used to ensure that a single 5'-end of the adapted target molecule is phosphorylated.

In other embodiments, phosphorylation is necessary for the subsequent ligation step. Phosphorylation of the primer, the adaptor or the single-stranded molecule following the strand separation step can be performed e.g., with the use of a polynucleotide kinase (PNK) such as T4 PNK.

Figure 2:
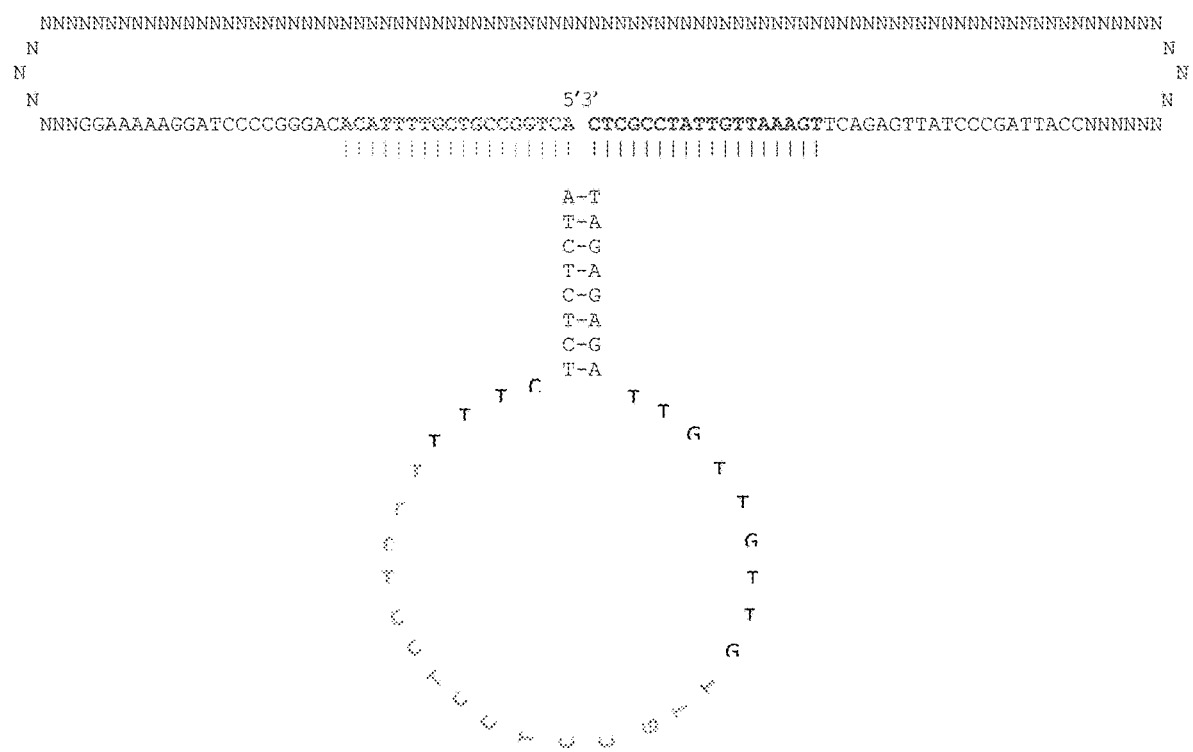
FIG. 2 shows step 1 of the method: annealing of the circularization probe.

In some embodiments, the ends of the nucleic acid (e.g., the 5'-end) comprise a modified nucleotide that protects the strand from nuclease digestion. In some embodiments, the strand comprises one or more phosphorothioate nucleotides. In some embodiments, the 3'-end of the nucleic acid comprises a modified nucleotide that blocks the 3'-end extension. In some embodiments, the strand comprises one or more inv-dT nucleotides In some embodiments, the method includes a step of annealing a circularization probe. This step includes contacting the 5'-phophorylated strand of the double stranded amplicon with a circularization oligonucleotide (probe) to generate a hybrid structure wherein the universal circularization sequences in the strand are hybridized to the circularization probe so that the ends of the strand are brought into ligatable proximity. (FIG. 2).

The general structure of the circularization oligonucleotide comprises two arms complementary to the circularization sequences in the amplicon (that have been introduced into the amplified target nucleic acid). The two arms are flanking a sequencing primer binding site.

In some embodiments, the circularization oligonucleotide has a structure shown FIG. 1 and in more detail, in FIGS. 2-6. The oligonudeotide comprises a stem-loop structure comprising the sequencing primer binding site in the loop, the stem-loop being flanked by arms complementary to the universal circularization sequences in the amplicon strand.

Figure 7:
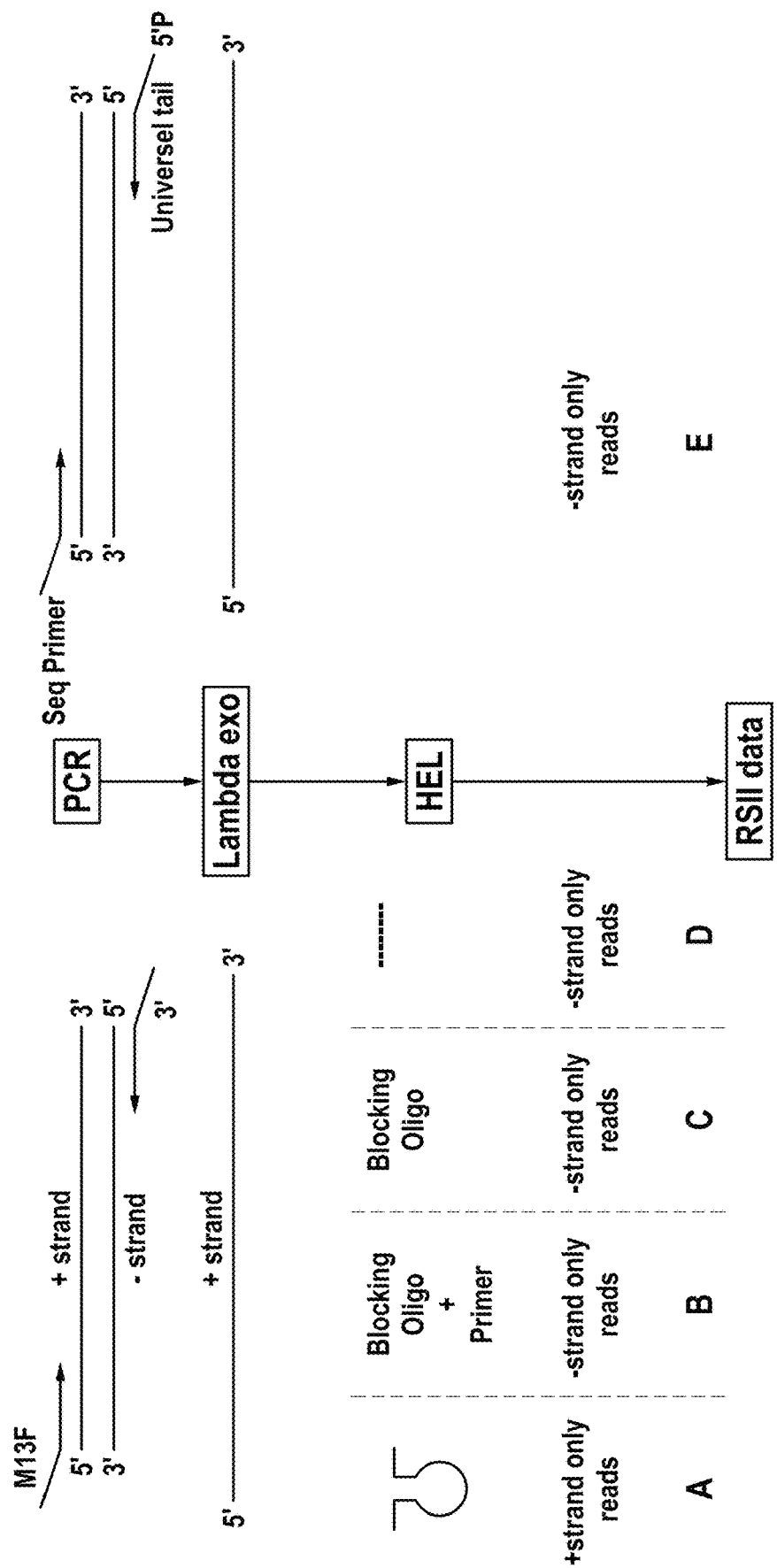
FIG. 7 shows diagrams of the HEL method with different structures of circularization oligonucleotides.

In other embodiments, the oligonucleotide comprises a linear segment comprising the sequencing primer binding site flanked by arms complementary to the universal circularization sequences in the amplicon strand. (FIGS. 7A, 7B, 7C, and 7D). The sequencing primer binding site is not complementary to the amplicon strand. The presence of the sequencing primer binding site creates a single-stranded region in the circular structure. (FIGS. 7B, 7C and 7D). In some embodiments, the sequencing primer binding sites are the sequences present in the circularization oligonudeotide. FIG. 7E.

Figure 3:
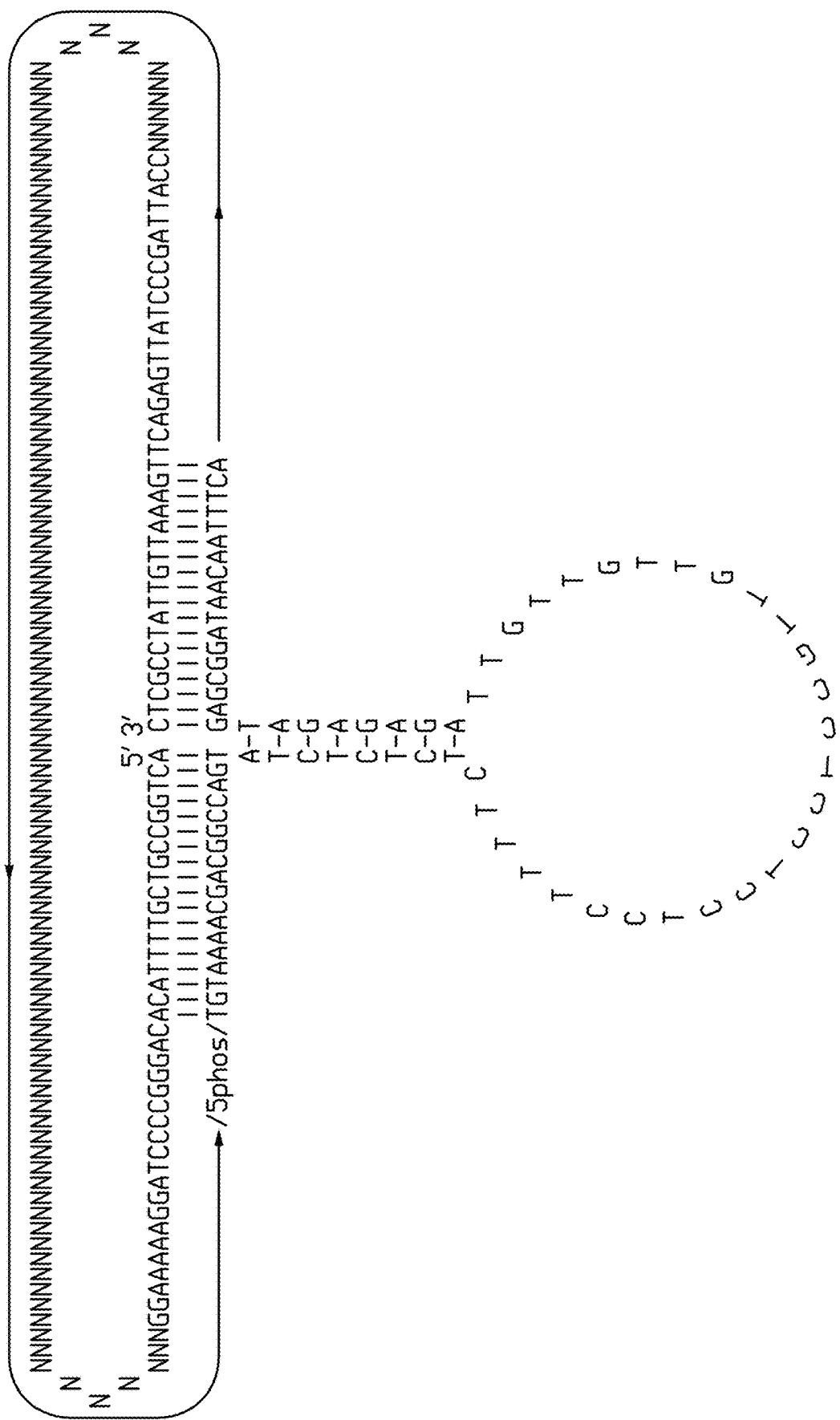
FIG. 3 shows step 2 of the method: strand extension.
Figure 4:
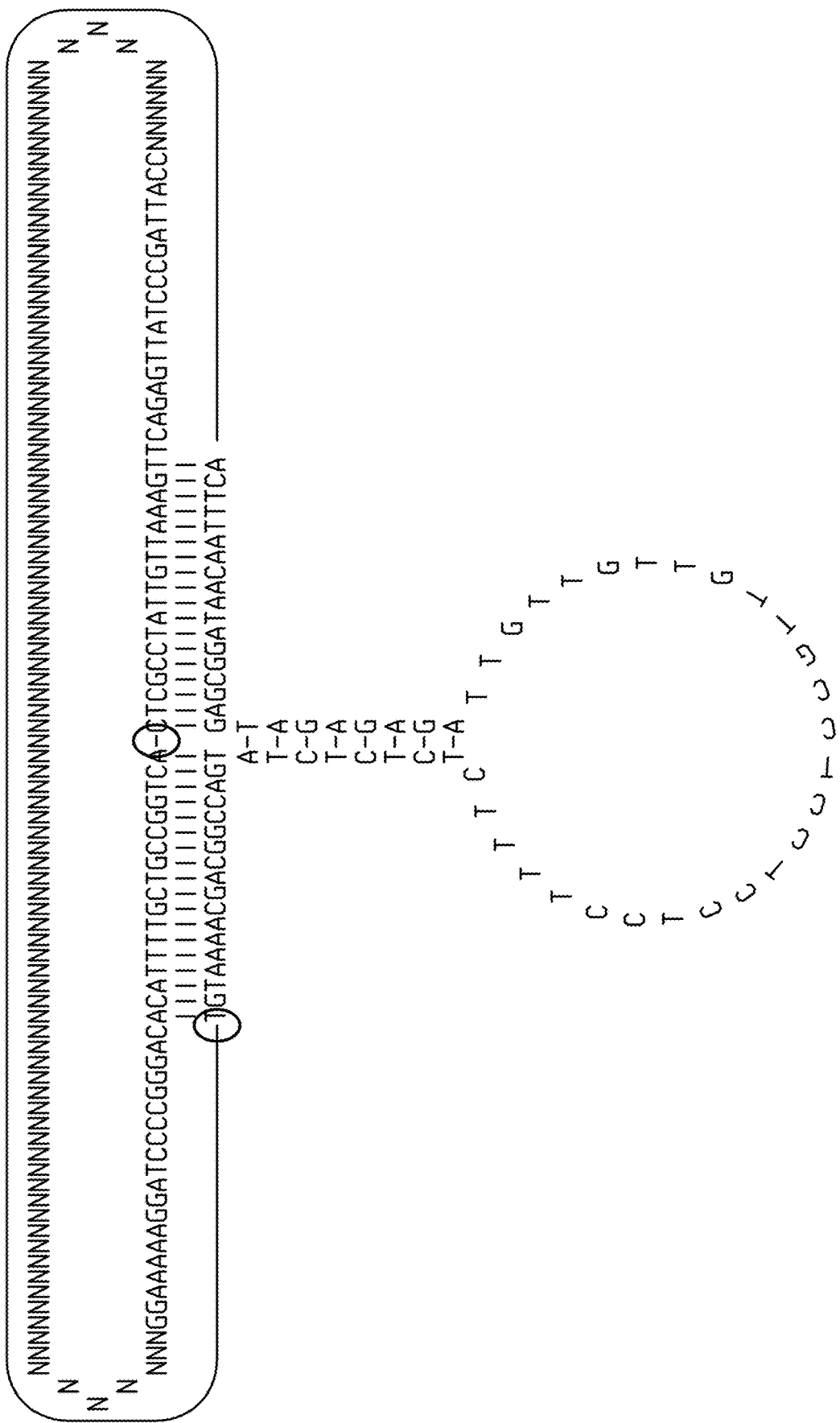
FIG. 4 shows step 3 of the method: ligation.

In some embodiments, the invention further comprises an extension step wherein the 3'-end of the circularization oligonucleotide is extended around the circularized target nucleic acid to reach the 5'-end of the circularization oligonucleotide thereby generating an extended strand. (FIGS. 3 and 7A).

In some embodiments, extension does not proceed from the circularization oligonucleotide but proceeds from a separate primer complementary e.g., to the universal sequence in the amplicon strand. (FIG. 7B).

Where the linear circularization oligonucleotide is used, two extensions occur during the extension step: an outer strand is extended to form a copy strand and the sequencing primer binding site is copied into the amplicon strand (FIGS. 7B, 7C and 7D). In one embodiment (FIG. 7B), the extension of the outer strand is done by adding a primer to initiate the extension and a blocking oligonucleotide to stop the extension before reaching the 5'end of circularization oligonucleotide. In another embodiment (FIG. 7C), the extension of the outer strand is initiated from the circularization oligonucleotide and a blocking oligonucleotide is used. In yet other embodiments (FIGS. 7D and 7E), the extension of the outer strand is initiated from the circularization oligonudeotide, and no blocking oligonucleotide is added to the reaction.

In some embodiments, the invention further comprises a ligation step comprising ligating the 5'- and 3'-ends of the extended copy strand thereby forming a circular molecule which is complementary to the target nucleic acid with universal sequences attached. (FIG. 4 and FIG. 7A. In other embodiments, ligation of the extended amplicon strand also takes place forming a circular molecule comprising the target nucleic acid with the sequencing primer binding site attached. (FIGS. 7B, 7C, 7D and 7E).

In some embodiments, the invention comprises an exonuclease digestion step wherein the linear nucleic acids possibly comprising excess oligonucleotides or un-circularized amplicons are removed from the reaction mixture. In some embodiments, the circularization oligonucleotides are removed with an exonuclease. (FIGS. 7B, 7C, 7D and 7E). In some embodiments, inhibitors of exonuclease progression are used. For example, phosphorothioates (PTA) are added to the circularization oligonucleotides order to prevent the digestion of the extended copy strand. (FIGS. 7C, 7D and 7E).

In some embodiments, the invention is a method of making a library of circular target nucleic acids. The method comprises an amplification step with universal primers. In some embodiments, universal primer binding sites are added to the nucleic acids in the sample, e.g., by adaptor ligation to create a library of adapted molecules. In some embodiments, universal sequences are present in the 5'-portion of target specific primers. The molecules in the library comprise target sequences flanked by universal sequence, e.g., universal primer binding site and a sequencing primer binding site. The circularization oligonucleotide may be complementary to the sequences contained in the adaptors. In other embodiments, the adaptors comprise only universal primer binding sites and universal primers introduce additional sequences not present in the adaptors. The universal primers may be bipartite amplification primers comprising a universal primer binding site and e.g., a sequencing primer binding site. The amplicons are then subjected to the steps of the method described above to generate a library of single stranded molecules. The final products are partially double stranded circular libraries that enable multi-pass sequencing reads of a single strand initiated from the sequencing primer binding site.

In some embodiments, the present invention comprises detecting target nucleic acids in a sample by nucleic acid sequencing. Multiple nucleic acids, including all the nucleic acids in a sample may be converted into the template configuration of the invention and sequenced. In some embodiments, the library of circular molecules described herein can be subjected to nucleic acid sequencing.

Sequencing can be performed by any method known in the art. Especially advantageous is the high-throughput single molecule sequencing. Examples of such technologies include the Illumina HiSeq platform (Illumina, San Diego, Calif.), Ion Torrent platform (Life Technologies, Grand Island, N.Y.), Pacific BioSciences platform utilizing the SMRT (Pacific Biosciences, Menlo Park, Calif.) or a platform utilizing nanopore technology such as those manufactured by Oxford Nanopore Technologies (Oxford, UK) or Roche Sequencing Solutions (Santa Clara, Calif.) and any other presently existing or future DNA sequencing technology that does or does not involve sequencing by synthesis. The sequencing step may utilize platform-specific sequencing primers. Binding sites for these primers may be introduced in the method of the invention as described herein, i.e., by being a part of adaptors or amplification primers. In some embodiments, the sequencing platform does not require a specific extension primer.

Figure 5:
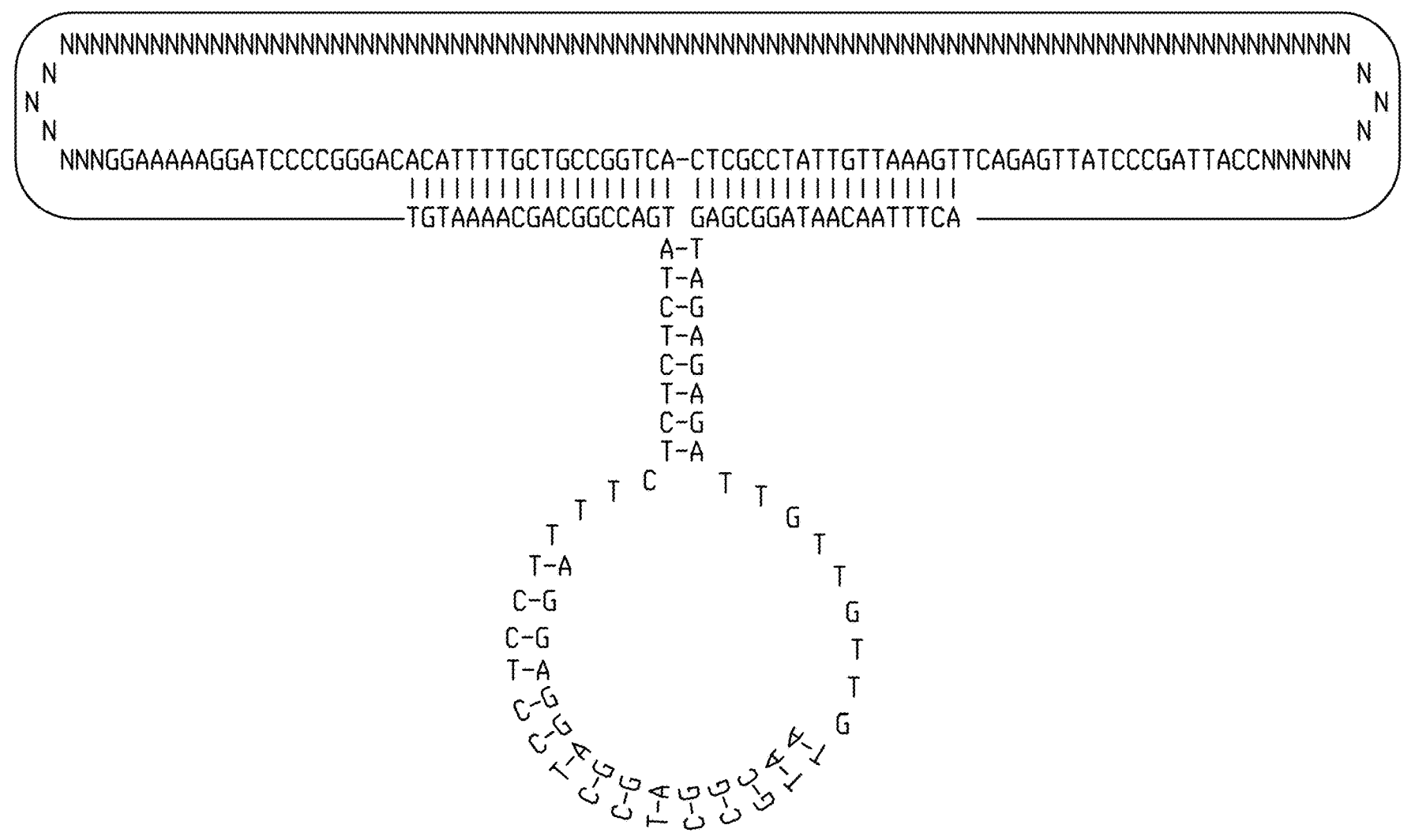

In some embodiments, the invention is a method of determining the sequence of a double-stranded target nucleic acid by primer extension. In this embodiment, the sequencing primer is annealed to the sequencing primer binding site present in the ligated strand (FIG. 5). Conveniently, the sequencing primer binding site is present in the single-stranded portion of the ligated strand comprising the stem-loop portion of the circularization oligonucleotide. The annealed sequencing primer is extended to generate a sequencing run of the ligated strand (FIG. 6 and FIGS. 7A, 7B, 7C, 7D and 7E).

Figure 6:
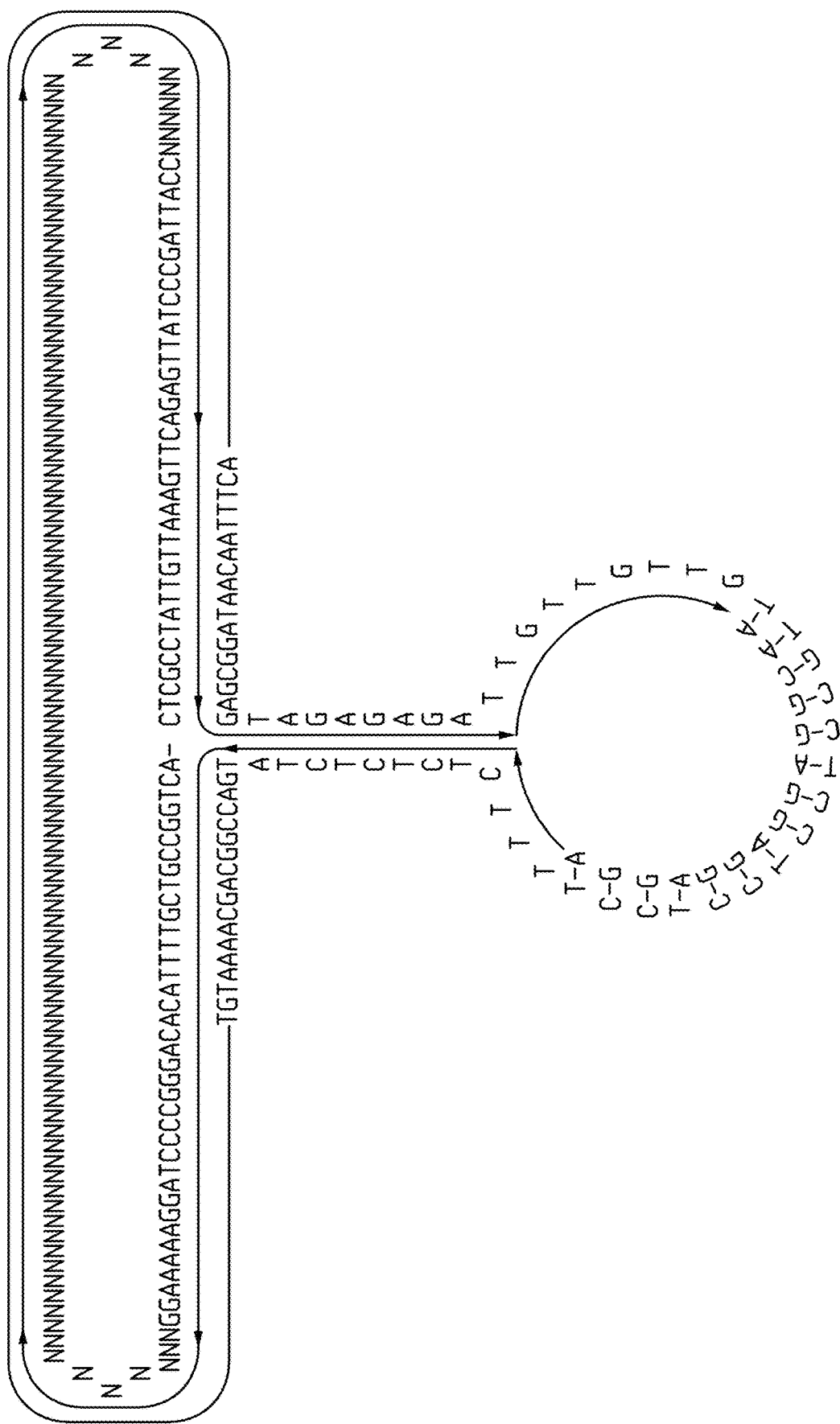
FIG. 6 shows step 5 of the method: extension of the sequencing primer (sequencing read).

Notably, the method of the invention is applicable to a wide variety of target nucleic acid sizes. In some embodiments, the target nucleic acid and the sequencing run illustrated in FIG. 6 is as short as 100 base pairs and as long as 10 kilobases.

Analysis and Error Correction

In some embodiments, the sequencing step involves sequence analysis including a step of sequence aligning. In some embodiments, aligning is used to determine a consensus sequence from a plurality of sequences, e.g., a plurality having the same barcodes (UID). In some embodiments barcodes (UIDs) are used to determine a consensus from a plurality of sequences all having an identical barcode (UID). In other embodiments, barcodes (UIDs) are used to eliminate artifacts, i.e., variations existing in some but not all sequences having an identical barcode (UID). Such artifacts resulting from PCR errors or sequencing errors can be eliminated.

In some embodiments, the number of each sequence in the sample can be quantified by quantifying relative numbers of sequences with each barcode (UID) in the sample. Each UID represents a single molecule in the original sample and counting different UIDs associated with each sequence variant can determine the fraction of each sequence in the original sample. A person skilled in the art will be able to determine the number of sequence reads necessary to determine a consensus sequence. In some embodiments, the relevant number is reads per UID ("sequence depth") necessary for an accurate quantitative result. In some embodiments, the desired depth is 5-50 reads per UID.

In some embodiments, the invention is a kit for performing the method of the invention. The kit comprises a first and second bipartite amplification primers comprising a target-binding sequence and optionally, universal sequence complementary to the circularization oligonucleotide; a circularization oligonucleotide at least partially complementary to both universal circularization sequences in the bipartite primers so that the ends of the strands comprising the bipartite primers can be brought ligatable proximity. The kit may also comprise a DNA ligase (in some embodiments, T4 DNA ligase, Taq DNA ligase, or E. coli DNA ligase is used), a polynucleotide kinase and a DNA polymerase, such as an amplification polymerase or a sequencing polymerase. Non-limiting examples of polymerases include prokaryotic DNA polymerases (e.g. Pol I, Pol II, Pol III, Pol IV and Pol V), eukaryotic DNA polymerase, archaeal DNA polymerase, telomerase, reverse transcriptase and RNA polymerase. Reverse transcriptase is an RNA-dependent DNA polymerase which synthesizes DNA from an RNA template. The reverse transcriptase family contains both DNA polymerase functionality and RNase H functionality, which degrades RNA base-paired to DNA.

In some embodiments, the DNA polymerase possesses strand displacement activity and does not have a 5'-3' exonuclease activity. In some embodiments, Phi29 polymerase and its derivatives are used, see U.S. Pat. Nos. 5,001,050, 5,576,204, 7,858,747 and 8,921,086. In some embodiments, the polymerase has the 3'-5' exonuclease activity that advantageously removes the 3'-A overhang from the amplicon strands.

EXAMPLES

Example 1

Circular Nucleic Acid Libraries Created Using a Stem-Loop Circularization Oligonucleotide In this example, a plasmid containing the 3.2 kb insert from the pol gene of the HIV-B reference was purified, linearized by restriction digestion and diluted to $10^8$ copies/mL for PCR amplification using one of the following pairs of forward (F) and reverse (R) primers. Only the reverse primers were phosphorylated at the 5'-end:

| Primer | SEQ ID NO: | Sequence |
|---|---|---|
| F | SEQ ID NO: 1 | ACTGGCCGTCGTTTTACACAGGGCCCCT AGGAAAAAGG |
| R | SEQ ID NO: 2 | /5Phos/GAGCGGATAACAATTTCACAG TCTCAATAGGGCTAATGG |
| F | SEQ ID NO: 3 | TCGGTGGTCGCCGTATCATTCAGGGCCC CTAGGAAAAAGG |
| R | SEQ ID NO: 4 | /5Phos/CAAGCAGAAGACGGCATACGA GATCAGTCTCAATAGGGCTAATGG |

Amplification was performed using the Phusion II HS High Fidelity DNA polymerase in a thermocycler according to the manufacturer's instructions.

The quality and quantity of the product was assessed using Fragment Analyzer or Bioanalyzer and Qubit dsDNA Broad Range. The product was purified using Kapa Purebead (KAPA BioScience, Cape Town, South Africa).

Single stranded DNA was generated using the Lambda exonuclease and incubating at 37° C. for 30 min followed by heat inactivation at 75° C. for 10 min. The product was purified using Kapa Purebead.

The ssDNA was phosphorylated with T4 Polynucleotide Kinase (PNK) by incubation 37 C for 30 min. followed by heat deactivation at 65 C for 20 min. The product was purified using Kapa Purebead.

Hybridization, extension and ligation were performed using the circularization oligonucleotide shown on FIG. 7A. First, the hairpin structure of the probe was generated using the following temperature profile:

20 ul of probe (stock at 100 uM)
80 ul of annealing buffer
2 min @ 80 C., ramp down to 25 C. at 2.5% ramp rate
Place @ 4 C. for immediate use (can be stored at −20 C. for 1 month)

The probe was mixed with the ssDNA from the previous step was mixed with Hifi Taq DNA Ligase or Taq DNA ligase and Phusion HS II DNA Polymerase and subjected to the following temperature profile

| Step | Temperature | Time |
|---|---|---|
| Denaturation | 95° C. | 5 min |
| hybridization, extension, ligation | 60° C. | 1 hour |
| Final Hold | 4° C. | Hold (∞) |

The quality and quantity of the product was assessed using Fragment Analyzer or Bioanalyzer and Qubit dsDNA Broad Range. The product was purified using Kapa Purebead.

Next, the circularized ssDNA was incubated with an exonuclease (Exo I and Exo III) for 30 min at 37C. The quality and quantity of the product was assessed using Fragment Analyzer or Bioanalyzer and Qubit dsDNA Broad Range. The product was purified using Kapa Purebead.

Example 2

Circular Nucleic Acid Libraries Created Using a Linear Probe

Hybridization, extension and ligation were performed using the circularization oligonucleotide shown on FIG. 7E.

PCR amplification, exonuclease digestion and DNA phosphorylation were performed essentially as in Example 1.

```
A linear probe used was
                                         SEQ ID NO: 5
5'GTGTAAAACGACGGCCAGTAAAAACGGAGGAGGAGGACAGTC*A*G*T*
A3'
*- phorphorothioate linkage
```

Annealing of the probe, ligation and extension (HEL) were performed essentially as in Example 1. The products of HEL were digested with T7 exonuclease and Exo I by incubating at 37° C. for 30 min. The quality and quantity of the product was assessed using Fragment Analyzer or Bioanalyzer and Qubit dsDNA Broad Range. The product was purified using Kapa Purebead.

Example 3

Circular Nucleic Acid Libraries Created Using a Linear Splint Probe

Hybridization, extension and ligation were performed using the circularization oligonudeotide shown on FIGS. 7B, 7C and 7D. The oligonudeotide has a splint sequence comprising a sequencing primer binding site.

PCR amplification, exonuclease digestion and DNA phosphorylation were performed essentially as in Example 1.

```
Probe (FIG. 7B) was
                                         SEQ ID NO: 6
5'GTAAAACGACGGCCAGTATCTCTCTCAACAACAACAACGGAGGAGGAGG AAAAGAGAGAGATGAGCGGATAACAATTTC/3InvdT/
```

Blocking oligo and primer were used

```
Blocking oligo
                                         SEQ ID NO: 7
CCTTTTTCCTAGGGGCCCT/3InvdT/

Primer
                                         SEQ ID NO: 8
CAGTCTCAATAGGGCTAATGG
```

Primer extension was performed using Phusion HiFi polymerase and the following temperature profile

| Denaturation | 95 | C. | 5 min |
|---|---|---|---|
| Hybridization | 55° | C. | 15 min |
| extension | 72° | C. | 15 min |
| hold | 4° | C. | hold |

The quality and quantity of the product was assessed using Fragment Analyzer or Bioanalyzer and Qubit dsDNA Broad Range. The product was purified using Kapa Purebead.

```
Probes (FIGS. 7C and 7D) was
                                         SEQ ID NO: 9
5'GTAAAACGACGGCCAGTATCTCTCTCAACAACAACAACGGAGGAGGAGG AAAAGAGAGAGATGAGCGGATAACAA*T*T*T*C3'
*- phorphorothioate linkage Blocking oligo was
                                         SED ID NO: 10
/5Phos/CCTTTTTCCTAGGGGCCCT/3InvdT/
```

Annealing of the probe, ligation and extension (HEL) were performed essentially as in Example 1 except blocking oligo was present as shown in FIGS. 7B and 7C. The products of HEL were digested with T7 exonuclease and Exo I as in Example 2. The quality and quantity of the product was assessed using Fragment Analyzer or Bioanalyzer and Qubit dsDNA Broad Range. The product was purified using Kapa Purebead.

Example 4

Sequencing the ssDNA Libraries

The DNA generated in Examples 1, 2 and 3 was sequenced on the Pacific BioSciences RSII instrument (Pacific BioSciences, Menlo Park, Calif.) according to the manufacturer's instructions.

Results are shown in FIG. 8. This graph represents the sequencing reads orientation obtained on the PB RSII platform for 5 circular libraries. The first library on top is a single stranded circular library and serves as a comparison for the 4 partially double stranded libraries named B, C, D & E (in reference to the previous figure). The single pass category correspond to the sequencing polymerase reads that went only once around the library template. Sequencing reads with −strand orientations are indicated in dark grey, and correspond to the expected orientation for this experimental design using +strand circular DNA templates. The three other categories of reads (double stranded, +strand only, −strand only) indicate multi-pass sequencing reads that went around the library template more than twice. The results show that the partially double stranded libraries yielded to a greater proportion of multi-pass reads of the expected orientation compared to the single-stranded circular library.

Example 4

Incorporating a Target-Capture Step into the Library Preparation

In this experiment, the target nucleic acids were enriched by target capture prior to the double-stranded Splint-HEL workflow. The panel of capture probes was design to target the loci currently being used for Carrier Screening applications designed to detect recessive genetic disease alleles in prospective parents. The capture probe panel (Roche Sequencing, Madison, Wisc.) had a total capture space of 112 kb and covered 20 conditions (26 genes)

| Disease | Gene |
| --- | --- |
| Alpha Thalassemia | HBA1/2 |
| Beta Thalassemia/Sickle Cell Anemia | HBB |
| Fragile X Syndrome | FMR1 |
| Spinal Muscular Atrophy | SMN1 |
| Cystic Fibrosis | CFTR |
| Bloom Syndrome | BLM |
| Canavan Disease | ASPA |
| Familial Hyperinsulinism | ABCC8 |
| Fanconi Anemia Group C | FANCC |
| Galactosemia Type 1, 2, 3 | GALT, GALK1, GALE |
| Gaucher's Disease | GBA |
| Glycogen Storage Disease Type 1a | G6PC |
| Joubert Syndrome | TMEM216 |
| Maple Syrup Urine Disease Type 1A/1B | BCKDHA, BCKDHB, DBT, DLD |

-continued

| Disease | Gene |
| --- | --- |
| Medium chain acyl-CoA dehydrogenase deficiency | ACADM |
| Mucolipidosis Type IV | MCOLN1 |
| Niemann-Pick Disease Type A/B | SMPD1 |
| Phenylketonuria | PAH |
| Smith-Lemli-Optiz Syndrome | DHCR7 |
| Tay-Sachs Disease | HEXA |

Isolated genomic DNA NA12878 was used as a model for human genomic DNA. Target capture was performed according to probe manufacturer's recommendations (SeqCap, Roche Sequencing, Madison, Wisc.). Using captured target DNA, short fragments were generated using fragmentase (Roche Sequencing, Cape Town, SA) to 250-300 bp for efficient circularization downstream using the Splint-HEL strategy. The libraries formed as shown on FIG. 7 (both the plus and minus strands). The libraries were sequenced on the RSII instrument (Pacific BioSciences, Menlo Park, Calif.). Results are shown below. 72-76% of the mapped consensus reads are on-target, as expected from capture experiments.

| Raw Reads | Mapped Consensus (% consensus) | On-target Consensus (% mapped consensus) |
| --- | --- | --- |
| 63897 | 44759 (96%) | 32256 (72%) |
| 68318 | 56338 (97%) | 41311 (73%) |
| 52234 | 39202 (98%) | 29272 (75%) |
| 44977 | 30809 (98%) | 23480 (76%) |

We claim:

1. A method of forming a circular molecule from a target nucleic acid in a sample, comprising:
   (a) amplifying the target nucleic acid with a first bipartite amplification primer and a second bipartite amplification primer comprising a universal circularization sequence and a target-specific sequence to generate double-stranded amplicons; wherein one of the first and second primers comprises a nuclease-targeting modification and the other primer comprises an exonuclease resistant modification;
   (b) contacting the amplicon with an exonuclease thereby removing one of the amplicon strands but not the other strand;
   (c) contacting the remaining strand of the amplicon with a circularization oligonucleotide comprising: (i) a 5'-phosphate, (ii) a single-stranded region, (iii) a double-stranded stem region, (iv) a single-stranded loop region comprising a sequencing primer binding site, (v) a single-stranded region, and (vi) an extendable 3'-end, to generate a hybrid structure wherein the universal circularization sequences in the amplicon are hybridized to the single-stranded regions (ii) and (v) of the circularization oligonucleotide;
   (d) contacting the sample with a DNA polymerase to extend the 3'-end of the circularization oligonucleotide to reach the 5'-end of the circularization oligonucleotide thereby generating a copy strand; and
   (e) contacting the sample with a DNA ligase to join the 3'-end and 5'-end of the copy strand thereby forming a circular nucleic acid molecule.

2. The method of claim 1, wherein the target nucleic acid comprises fragments of a genome selected from cell-free plasma DNA, sonicated DNA, and restriction digested DNA.

3. The method of claim 1, wherein the circularization oligonucleotide comprises a ligand for a capture moiety.

4. The method of claim 1, wherein the target nucleic acid is enriched prior to step (a).

5. A method of making a library of circular target nucleic acids according to claim 1, comprising:
   (a) amplifying a plurality of different target nucleic acids with first and second bipartite amplification primers comprising a universal circularization sequence and a corresponding target-specific sequence to generate a plurality of different double-stranded amplicons; wherein one of the first and second primers comprises a nuclease-targeting modification and the other primer comprises an exonuclease resistant modification; and
   (b) subjecting the amplicons of step (b)-(e) of claim 1.

6. A method of determining the sequence of a double-stranded target nucleic acid in a sample comprising:
   (a) forming circular nucleic acids by a method of claim 1;
   (b) contacting the sample with a sequencing primer complementary to the sequencing primer binding site; and
   (c) extending the sequencing primer with a nucleic acid polymerase thereby determining the sequence of the target nucleic acid.

7. A method of determining the sequence of a double-stranded target nucleic acid in a sample comprising:
   (a) forming circular nucleic acids by a method of claim except omitting a sequencing primer binding site from the circularization oligonucleotide; and
   (b) extending the circularization oligonucleotide with a nucleic acid polymerase thereby determining the sequence of the target nucleic acid.

8. A kit for determining the sequence of a target nucleic acid comprising:
   (a) a first bipartite amplification primer and a second bipartite amplification primer comprising a universal circularization sequence and a target-binding sequence, wherein one of the first and second primers comprises a nuclease-targeting modification and the other primer comprises an exonuclease resistant modification;
   (b) a circularization oligonucleotide comprising (i) a 5'-phosphate, (ii) a single-stranded region, (iii) a double-stranded stem region, (iv) a single-stranded loop region comprising a sequencing primer binding site, (v) a single-stranded region, and (vi) an extendable 3'-end;
   (c) a DNA polymerase; and
   (d) a DNA ligase.

* * * * *

SEQUENCE LISTING

<160> NUMBER OF SEQ ID NOS: 10

<210> SEQ ID NO 1
<211> LENGTH: 38
<212> TYPE: DNA
<213> ORGANISM: Artificial Sequence
<220> FEATURE:
<223> OTHER INFORMATION: single stranded

<400> SEQUENCE: 1
actggccgtc gttttacaca gggcccctag gaaaaagg                                38

<210> SEQ ID NO 2
<211> LENGTH: 39
<212> TYPE: DNA
<213> ORGANISM: Artificial Sequence
<220> FEATURE:
<223> OTHER INFORMATION: single stranded

<400> SEQUENCE: 2
gagcggataa caatttcaca gtctcaatag ggctaatgg                               39

<210> SEQ ID NO 3
<211> LENGTH: 40
<212> TYPE: DNA
<213> ORGANISM: Artificial Sequence

```
<220> FEATURE:
<223> OTHER INFORMATION: single stranded

<400> SEQUENCE: 3
tcggtggtcg ccgtatcatt cagggcccct aggaaaaagg                        40

<210> SEQ ID NO 4
<211> LENGTH: 45
<212> TYPE: DNA
<213> ORGANISM: Artificial Sequence
<220> FEATURE:
<223> OTHER INFORMATION: single stranded

<400> SEQUENCE: 4
caagcagaag acggcatacg agatcagtct caatagggct aatgg                  45

<210> SEQ ID NO 5
<211> LENGTH: 45
<212> TYPE: DNA
<213> ORGANISM: Artificial Sequence
<220> FEATURE:
<223> OTHER INFORMATION: single stranded

<400> SEQUENCE: 5
gtgtaaaacg acggccagta aaaacggagg aggaggacag tcagt                  45

<210> SEQ ID NO 6
<211> LENGTH: 79
<212> TYPE: DNA
<213> ORGANISM: Artificial Sequence
<220> FEATURE:
<223> OTHER INFORMATION: single stranded

<400> SEQUENCE: 6
gtaaaacgac ggccagtatc tctctcaaca acaacaacgg aggaggagga aaagagagag  60
atgagcggat aacaatttc                                              79

<210> SEQ ID NO 7
<211> LENGTH: 19
<212> TYPE: DNA
<213> ORGANISM: Artificial Sequence
<220> FEATURE:
<223> OTHER INFORMATION: single stranded

<400> SEQUENCE: 7
ccttttccct aggggccct                                              19

<210> SEQ ID NO 8
<211> LENGTH: 21
<212> TYPE: DNA
<213> ORGANISM: Artificial Sequence
<220> FEATURE:
<223> OTHER INFORMATION: single stranded

<400> SEQUENCE: 8
cagtctcaat agggctaatg g                                           21

<210> SEQ ID NO 9
<211> LENGTH: 79
<212> TYPE: DNA
<213> ORGANISM: Artificial Sequence
<220> FEATURE:
<223> OTHER INFORMATION: single stranded

<400> SEQUENCE: 9
```

```
gtaaaacgac ggccagtatc tctctcaaca acaacaacgg aggaggagga aaagagagag      60
atgagcggat aacaatttc                                                  79

<210> SEQ ID NO 10
<211> LENGTH: 19
<212> TYPE: DNA
<213> ORGANISM: Artificial Sequence
<220> FEATURE:
<223> OTHER INFORMATION: single stranded

<400> SEQUENCE: 10 ccttttcct aggggccct                                                   19
```